United States Patent [19]

Woolard

[11] Patent Number: 4,909,834
[45] Date of Patent: Mar. 20, 1990

[54] 1-TRIFLUOROMETHYLPHENYL-2-PHENYLIMINOPYRROLIDINES AND THEIR USE AS HERBICIDES

[75] Inventor: Frank X. Woolard, Richmond, Calif.

[73] Assignee: ICI Americas Inc., Wilmington, Del.

[21] Appl. No.: 290,247

[22] Filed: Dec. 27, 1988

[51] Int. Cl.⁴ .................. A01N 43/36; C07D 207/22
[52] U.S. Cl. .......................................... 71/95; 548/559
[58] Field of Search ............................ 548/559; 71/95

[56] References Cited

U.S. PATENT DOCUMENTS

| | | | |
|---|---|---|---|
| 3,132,151 | 5/1964 | Bortnick et al. | 548/559 |
| 4,077,981 | 3/1978 | Enders et al. | 548/559 |
| 4,110,105 | 8/1978 | Teach | 71/95 |
| 4,210,589 | 7/1980 | Teach | 548/543 |
| 4,645,843 | 2/1987 | Broadhurst et al. | 548/543 |

OTHER PUBLICATIONS

Kwok and Pranc, *Journal of Organic Chemistry* vol. 32 No. 3 (1963), pp. 738–740.

*Primary Examiner*—Joseph Paul Brust
*Assistant Examiner*—MarySue Howard
*Attorney, Agent, or Firm*—Michael J. Bradley

[57] ABSTRACT

1-Trifluoromethylphenyl-2-(substituted phenyl)iminopyrrolidines of the formula

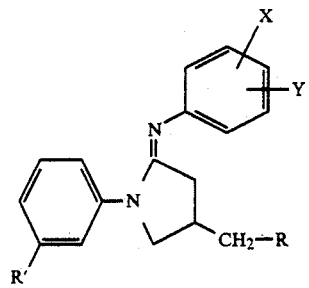

in which R is H, halogen, or $C_1$–$C_4$ alkyl; R' is $CF_3$, $CH_3$, $CF_2CHF_2$, $OCF_2CHF_2$, $OCHF_2$, $OCF_3$, $SCH_3$, $S(O)CH_3$, $SO_2CH_3$, methoxyiminomethyl, methoxyimino-1-ethyl, benzoyloxyiminomethyl, and benzoyloxyimino-1-ethyl; and X and Y are independently H, halogen, CN or $CF_3$, are useful as herbicidal agents.

30 Claims, No Drawings

1-TRIFLUOROMETHYLPHENYL-2-PHENYLIMINOPYRROLIDINES AND THEIR USE AS HERBICIDES

BACKGROUND AND SUMMARY OF THE INVENTION

This invention relates to certain substituted 1-trifluoromethylphenyl-2-phenyliminopyrrolidines and to their use in herbicidal formulations. In particular, this invention relates to substituted 1-trifluoromethylphenyl-2-phenyliminopyrrolidines of the formula

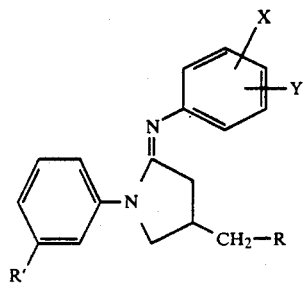

in which:

R is a member selected from the group consisting of H, halogen, and $C_1$-$C_4$ alkyl: $R_1$ is a member selected from the group consisting of $CF_3$, $CH_3$, $CF_2CHF_2$, $OCF_2CHF_2$, $OCHF_2$, $OCF_3$, $SCH_3$, $S(O)CH_3$, $SO_2CH_3$, methoxyiminomethyl, methoxyimino-1-ethyl, benzoyloxyiminomethyl, and benzoyloxyimino-1-ethyl: and X and Y are independently selected from the group consisting of H, halogen, CN and $CF_3$.

The compounds of the present invention, as will be seen from the description and test data which follow, have utility as both pre-emergence and post-emergence herbicides, against a wide range of plant species. These compounds are of particular utility in the control of weeds associated with wheat crops. The preferred method of application is pre-emergence.

The terms "herbicide" and "herbicidal" are used herein to denote the inhibitive control or modification of undesired plant growth. Inhibitive control and modification include all deviations from natural development such as, for example, total killing, growth retardation, defoliaiion. desiccation, regulation, stunting, tillering, stimulation, leaf burn, and dwarfing. The term "herbicidally effective amount" is used to denote any amount which achieves such control or modification when applied to the undesired plants. themselves or to the area in which these plants are growing. The term "plants" is intended to include germinant seeds, emerging seedlings and established vegetation, including both roots and above-ground portions.

DETAILED DESCRIPTION OF THE INVENTION AND PREFERRED EMBODIMENTS

Within the scope of the above formula, certain embodiments are preferred, as follows.

R is preferably H, halogen or methyl. Among the halogens, chloro, bromo ahd fluoroaare preferred, with chloro and fluoro particilarly preferred, and chloro the most preferred. The most preferred R groups are chloro and methyl.

R is preferably $CF_3$.

X and Y may be the same or different are preferably H, chooro, bromo, fluoro, CN or $CF_3$. Of these, H, chloro, fluoro, CN and $CF_3$ are the most preferred.

X itself is preferably H or halogen, more preferably H, chloro, or fluoro, and most preferably H.

Y itself is prfferably H, chloro, fluoro, CN or CF, with chloro, fluoro, CN and $CF_3$, the most preferred.

The term "alkyl" is intended to nnclude both straight-chain and branched-chain groups.

It will be noted that the generic formula indicates a chiral center at the 4-position of the pyrrolidine ring. The various compounds disclosed herein as examples of compounds within the generic formula each represent a mixture of enantiomers at the 4-position. Herbicidal activity for the mixture is an indication of herbicidal activity for each individual enantiomer. It is to be expected however that in certain cases one enantiomer will have a greater herbicidal activity than the other.

The compounds of the present invention may be prepared by a variety of synthesis routes. For those compounds where R is chloro. the sequence is first begun by the preparation of a 3-halo-4-chloromethyl-1-(trifluoromethylphenyl)-2-pyrrolidone with the ultimately desired substituents for the radical R already attached to the methyl group. This is done by the catalytic intramolecular cyclization of an α-halogen-containing N-2-alkenyl amide using a transition metal halide catalyst in a mixture of a hydrocarbon solvent. preferably toluene. and a dialkyl amine, preferably di-n-propyl or di-n-butyl amine according to the process described in Broadhurst. U.S. Pat. No. 4,132,713 (Jan. 2, 1979) or that described in Broadhurst. et al., U.S. Pat. No. 4,645,843 (Feb. 24, 1987). both of which are incorporated herein by reference. The product 3-halo-4-chloro-methyl-1-(3-trifluoromethylphenyl)-2-pyrrolidone is then treated with zinc/copper couple in refluxing ethanol or methanol to replace the halogen at the 3-position with hydrogen.

The resulting pyrrolidone is then treated with an excess of diphssphorus decasulfide (200–250 mol) in dry tetrahydrofuran at a temperature between about 20° C. and the reflux temperature of the mixture. which will generally be around 65° C. The thione thus prepared is dissolved in an aprotic solvent much as ethylene dichloride. chloroform, ethyl acetate. or preferably methylene chloride. with about 200 mol % of an rromatic amine. The temperature of the solution is maintained at 0–15° C. and a solution of an oxidant such as peracetic acid or. preferably. m-chloroperoxybenzoic acid in the same solvent is added dropwise at such a rate that the temperature does not exceed 15° C. When the addition is complete. the reaction mixture is processed according to conventional techniques to extract the crude product. The latter is then purified by chromatoraphy on silica gel using mixtures of ethyl acetate/hexanes as eluants.

For those compounds where R is methyl or other alkyl. the starting material is 4-alkyl-1-(3-trifluoromethylphenyl)-2-pyrrolidone prepared from 3-chloro-4-alkyl-1-(3-trifluoromethylphenyl)-2-pyrrolidone in a manner identical to the preparation of 4-chloromethyl-1-(3-trifluoromethyl-phenyl)-2-pyrrolidone. The procedure then continues in a sequence analogous to that described above. In an alternative procedure, the alkyl-substituted product may be prepared directly from the 4-alkyl-1-(trifluoromethylphenyl)-2-pyrrolidone by combining the latter with approximately 105 mol % of an aromatic amine in the presence of polyphosphoric acid trimethyl ester. the latter having been prepared from 200 mol % (based on the pyrrolidone) of phosphorus pentoxiee and 400 mol % of heaamethyldisiloxane. Heating the resulting mixture to a temperature of about 160-190° C. for about 36-60 hours provides product yields of about 50-85.

The following are examples of compounds which have been synthesized by the procedures described above. These examples are offered strictly for purpose of illustration. and are intended neither to limit nor to define the invention in any manner.

EXAMPLE 1

The example illustrates the preparation of 1-(3-trifluoromethylphenyl)-2-(4-cyanophenylimino)-4-chlorometh-ylpyrrolidine in which according to the generic formula given above, the trifluoromethyl group is in the meta-position. R is Cl, X is H. and Y is 4-CN. This compound is shown in Table I below asccompound no. 8.

The starting material for this compound was 3-chloro-4-chloromethyl-1-(3-trifluoromethylphenyl)-2-pyrrolidone. prepared according to the procedure described in Broadhurst. et al.. U.S. Pat. No. 4,645,843.

A 250-mL Erlenmeyer flask was charged with 24.43 g (0.37 gram-atoms) of zic metal and 70 mL of 3% aqueous HCl. The resulting suspension was swirled for a few minutes. then decanted. The metal was washed twice more with 70-mL portion of 3% HCl. followed by three 100-mL portions of water. As much water as possible was then decanted. and the metal was washed with two 50-mL portions of 2% $CuSO_4$ solution. The blue color was allowed to disappear prior to each decanting of the liquid.

The black metal was then tansferred to a 1000-mL threenecked round-bottomed flask equipped with a heating mantle. mechanical stirrer. and reflux condenser. To this was then added 50.00 g (0.16 mole) of 1-(3-trifluoromethyl-phenyl)-3-chloro-4-chloromethyl-2-pyrrolidone in 300 mL of absolute ethanol. in a single portion. The resulting suspension was then stirred and heated to reflux. After 2.5 hours, silica gel thin-layer chromatography (TLC) (1:1 ethyl acetate/hexanes) showed the reaction to be complete.

Vacuum filtration through a pad of diatomaceous earth followed by removal of the ethanol under reduced pressure provided an iil that was partitioned between water (250 mL) and ethyl acetate (100 mL). The layers were separated and the aqueous phase washed with two 50-mL portions of ethyl acetate. The organic layers were combined and dried ($MgSO_4$). and the solvent removed under reduced pressure to afford 41.44 g (93%) of 1-(3-trifluoromethylphenyl)4-chloromethyl-2-pyrrolidone as atan-yellow syrup.

The latter was then converted to the thione as follows. A 500-mL boiling flask equipped with a magnetic stirrer. heating mantle and reflux condenser carrying a nitrogen bubbler was chareed with 12.20 g (43.9 mmol) of the pyrrolidone. 200 mL of freshly distilled (sodium/benzophenone) tetrahydrofuran (THF). and 19.53 g (89.9 mmol) of $P_4S_{10}$. The solution was stirred and heated to reflux. After four hours. analysis by capillary gas chromatography (GC) showed the reaction to be 84% complete. A second portion of $P_4S_{10}$ (5.00 g. 22.5 mmol) was then added and the refluxing continued for an additional two hours. The resulting suspension was then cooled to room temperature, and then vacuum filtered through a pad of diatomaceous earth. The THF was then removed under reduced pressure. Flash chromatography of the residual oil on silica gel with 1:1 ethyl acetate/hexanes as eluant afforded 10.50 g (81%) of 1-(3-trifluoromethylphenyl)-4-chloromethyl-2-pyrrolidone thione as an odorous yellow oil.

The thione was then converted to the final product as follows. A 200-mL three-necked round-bottomed flask equipped with a magnetic stirrer, thermometer, and pressure equalizing addition funnel carrying a nitrogen bubbler was charged with 2.00 g (6.8 mmol) of the thione. 1.63 g (13.8 -mmol) of 4-amnnobenzonitrile. and 25 mL of methylene chloride. The solution was stirred and cooled to 0° C. by immersing the flask in an ice bath. A solution of 4.70 g (27.2 -mmol) of m-chlorobenzoic acid in 75 mL of methylene chloride was then added dropwise at such a rate that the temperature did not rise above 5° C. (25 minutes total). The methylene chloride was removed under reduced pressure and the residual solid dissolved in 50 mL of ethyl acetate. The solution was washed with two 25-mL portions of saturated sodium carbonate solution. followed by two 25-mL portions of water. then dried ($MgSO_4$). and the solvent removed in vacuo. Chromatography of the residual oil on silica gel with 15% ethyl acetate/hexanes as eluant provided 0.80 g (32%) of the product as a very thick yellow syrup.

The structure of the product was confirmed as that of 1-(3-trifluoromethylphenyl)-2-(4-cyanophenylimino)-4-chloromethylpyrrolidine by infrared spectroscopy (IR), mass spctrometry (MS) and nuclear magnetic resonance (NMR).

EXAMPLE 2

This example illustrates the preparation of 1-(3-trifluoromethylphenyl)-2-(4-cyanophenylimino)-4-ethyl-pyrrolidine in which. according to the generic formula given above. the trifluoromethyl group is in the meta-position, R is $CH_3$, X is H. and Y is 4-CN. This compound is shown in Table I below as compound no. 11.

The starting material for this compound was 1-(3-trifluoromethylphenyl)-3-chloro-4-ethyl-2-pyrrolidone, prepared according to a proceuure analogous to that described in Broadhurst. et al., U.S. Pat. No. 4,645,843. Using a procedure identical to that described in Example 1, this compound was converted to 1-(3-trifluoromethylphenyl)-4-ethyl-2-pyrrolidone. then to 1-(3-trifluoromethylphenyl)-4-ethyl-2-pyrrolidone thione. and finally to the desired product in the form of crystals having a melting point range of 109-111° C. The structure was confirmed as that of 1-(3-trifluoromethylphenyl)-2-(4-cyanophenylimino)-4-ethylpyrrolidine by IR. MS and NMR.

EXAMPLE 3

This example illustrates the preparation of 1-(3-trifluoromethylphenyl)-2-(3-trifluoromethylphenylimino)-4-ethylyrrolidine in which, according to the generic formula given above, the trifluoromethyl group is in the meta-position. R is $CH_3$, X is H, and Y is 3-$CF_3$ This compound is shown in Table I below as compound no. 13.

The starting material for this preparation was 1-(3-trifluoromethylphenyl)-3-chloro-4-ethyl-2-pyrrolidone, prepared according to the procedure described in Broadhurst. et al., U.S. Pat. No. 4,645,843. which was converted to 1-(3-trifluoromethylphenyl)-4-ethyl-2-pyrrolidone using the procedure described in Example 1.

The latter was then converted to the final product as follows. A 100-mL boiling flask equipped with a magnetic stirrer and reflux condenser carrying a nitrogen bubbler was charged with 1.42 g (10.0 mmol) of phosphorus pentoxide and 4.25 mL (3.25 g. 20.0 mmol) of hexamethyldisiloxane. The suspension was stirred and the flask immersed in an oil bath maintained at 160° C. When the mixture began to refuux. 1.29 g (5.0 mmol) of the pyrrolidone and 0.65 mL (0.84 g. 5.2 mmol) of 3-aminobenzotrifluoride were added all at once. After an additional hour of heating with stirring at 160° C., the mixture was homogeneous. After a total of 40 hours under such conditions. the mixture was allowed to cool to room temperature and partitioned between 25 mL each of 2N NaOH and ethy acetate.

The resulting layers were separated and the aqueous phase was extracted with 25 mL of ethyl acettte. The organic phases were combined and dried (MgSO$_4$), and the solvent removed under reduced pressure to give a dark oil. Chromatography on silica gel with 30% ethyl acetate/hexanes as eluant provided 1.57 g (78%) of product as a thick orange-yellow syrup. The structure of the product was confirmed as that of 1-(3-trifluoromethylphenyl)-2-(3-trifluoromethyl-phenylimino)-4-ethylpyrroiidine by IR. MS and NMR.

These and further compounds prepared by similar procedures are listed in Table I below. together with physical data in the form of melting point ranges where such measurements were possibly and physical descriptions of the product where neither melting points nor refractive indices could be taken.

TABLE I
COMPOUNDS

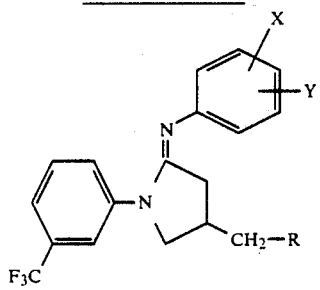

| No. | R | X | Y | m.p. (°C.) or description |
|---|---|---|---|---|
| 1 | Cl | H | H | waxy solid |
| 2 | Cl | H | 3-CN | waxy solid |
| 3 | Cl | H | 4-CF$_3$ | waxy solid |
| 4 | Cl | H | 3-CF$_3$ | thick syrup |
| 5 | Cl | H | 2-Cl | waxy solid |
| 6 | Cl | H | 3-Cl | thick syrup |
| 7 | Cl | H | 4-Cl | 108-110 |
| 8 | Cl | H | 4-CN | waxy solid |
| 9 | Cl | 3-F | 4-F | thick syrup |
| 10 | Cl | 3-Cl | 4-F | thick syrup |
| 11 | CH$_3$ | H | 4-CN | 109-111 |
| 12 | CH$_3$ | H | 4-F | 100-104 |
| 13 | CH$_3$ | H | 3-CF$_3$ | thick syrup |
| 14 | CH$_3$ | H | H | thick syrup |

The compounds listed in the foregoing table were tested for herbicidal activity by various methods and at various rates of application. The results of some of these tests are given below. As one skilled in the art is aware, the results obtained in herbicidal screening tests are affected by a number of factors that are not readily controllable. Environmental conditions such as amount of sunlight and water, soil type, soil pH, temperature and humidity, are examples of such factors. The depth of planting and the application rate of the herbicide, as well as the nature of crops being tested, can also affect the test results. Results will also vary from crop to crop and within the crop varieties.

The test procedures used are as follows:

Pre-Emergence Herbicidal Evaluation

Planting flats were filledwith sandy loam soil containing a fungicide and fertilizer. The soil was leveled and rows of grassy weeds. broadleaf weeds and yellow nutsedge sedge (*Cyperus esculentus*), were planted thickly enough so that several seedlings emerged per inch of row. The grassy weeds were yellow foxtail (*Setaria veridis*), watergrass (*Echinochloa crusgalli*) and wild oat (*Avena fatua*), Broadleaf weeds utilized were annual morningglory (*Ipomoea purpurea*), velvetleaf (Abutilon theophrasti), wild mustard (*Brassica kaber*), and curly dock (*Rumex crispus*).

Solutions of the test compounds were made by weighing out 333 mg o the test compound into a 60-mL wide-mouth bottle. then dissolving the compound in 25 mL of acetone containing 1% Tween® 20 (polyoxyethylene sorbitan monolaurate emulsifier). Additional solvents, not exceeding 5 mL, were used if needed to dissolve the compound. A 20.5-mL aliquot was then taken from the solution and diluted with 25 mL of an acetone:water mixture (19:1) containing 1% Tween® 20. This was used as the spray solution.

One day after planting, the flats were sprayed with the spray solution at a rate of 80 gallons of solution per acre with th compound being applied at a rate of 4 pounds per acre (4.48 kg/ha).

The flats were then returned to the greenhouse and watered daily by sprinkling. The degree of weed control was estimated and recorded 3 weeks after treatment, as percentage control compared to the growth of the same species in an untreated check flat of the same age.

The percent control is the total injury to the plants due to all factors, including inhibited germination, killing of the plant tissue after emergence, stunting, malformation, chlorosis, and other types of injury. The control ratings vary from 0 to 100 percent, where 0 represents no effect with growth equal to the untreated control. and 100 represents complete kill; a dash indicates that no test was performed at that level of application.

Post-Emergence Herbicidal Evaluation

The soil was prepared and seeded with the same varieties used in the pre-emergence test. The flats were placed in the greenhouse at 70-85° F. (21°-29° C.) and watered by sprinkling. Twelve to fourteen days after planting, the flats were sprayed at a rate of 80 gallons of solution per acre. Each compound was applied at the rate of 4 pounds/acre (4.48 kg/ha), using a spray solution prepared as in the pre-emergence test.

The flats were returned to the greenhouse after spraying and watered daily without wetting the foliage. Three weeks after treatment the degree of weed control was estimated and recorded as percentage control compared to the growth of the same species in an untreated check flat of the same age. The percent control ratings were assigned on the same basis as for the pre-emergence evaluation.

The following table lists the results of these tests, in terms of averages for the grasses and broadleaf weeds, with yellow nutsege listed separately, in both pre- and post-emergence evaluations.

TABLE II

HERBICIDE TEST RESULTS – PERCENT CONTROL AT 4 LB/ACRE

| Compound No. | Pre-Emergence | | | Post-Emergence | | |
| --- | --- | --- | --- | --- | --- | --- |
| | YNS | AVG | AVB | YNS | AVG | AVB |
| 1 | 0 | 28 | 21 | 0 | 0 | 8 |
| 2 | 0 | 50 | 48 | 0 | 0 | 8 |
| 3 | 0 | 48 | 50 | 0 | 2 | 35 |
| 4 | 0 | 55 | 58 | 0 | 38 | 61 |
| 5 | 0 | 0 | 0 | 0 | 0 | 3 |
| 6 | 0 | 55 | 31 | 0 | 0 | 28 |
| 7 | 0 | 32 | 0 | 0 | 0 | 24 |
| 8 | 20 | 72 | 76 | 0 | 48 | 38 |
| 9 | 0 | 67 | 54 | 0 | 60 | 65 |
| 10 | 0 | 62 | 69 | 0 | 48 | 80 |
| 11 | 0 | 83 | 98 | 0 | 37 | 67 |
| 12 | 0 | 83 | 98 | 0 | 37 | 53 |
| 13 | 0 | 97 | 80 | 0 | 80 | 100 |
| 14 | 0 | 83 | 80 | 0 | 17 | 88 |

Abbreviations:
YNS: Yellow Nutsedge
AVG: Grasses averaged
AVB: Broadleaf weeds averaged The compounds of the present invention are useful as herbicides and can be applied in a variety of ways known to those skilled in the art, at various concentrations. In practice, the compounds are applied as formulations containing the various adjuvants and carriers known to or used in the industry for facilitating dispersion. The choice of formulation and mode of application for any given compound may affect its activity, and selection will be made accordingly. The compounds of the invention may thus be formulated as granules, as wettable powders, as emulsifiable concentrates, as powders or dusts, as flowables, as solutions, suspensions or emulsions, or in controlled-release forms such as microcapsules. These formulations may contain as little as about 0.5% to as much as about 95% or more by weight of active ingredient. The optimum amount for any given compound will depend upon the nature of the seeds or plants to be controlled. The rate of application will generally vary from about 0.01 to about 10 pounds per acre, preferably from about 0.02 to about 4 pounds per acre.

Wettable powders are finely divided particles which disperse readily in water r other liquid carriers. The particles contain the active ingredient retained in a solid matrix. Typical solid matrices include fuller's earth. kaolin clays, silicas and other readily wet organic or inorganic solids. Wettable powders normally contain about 5% to about 95% oft the active ingredient plus a small amount of wetting, dispersing, or emulsifying agent.

Emulsifiable concentrates are homogeneous liquid compositions dispersible in water or other liquid, and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from about 0.5% to about 95% of the concentrate.

Granular formulations include both extrudates and relatively coarse particles, an are usually applied without dilution to the area in which suppression of vegetation is desired. Typical carriers for granular formulations include sand, fuller's earth, attapulgite clay, bentonite clays, montmorillonite clay, vermiculite, perlite and other organic or inorganic materials which absorb or which can be coated with the active compound. Granular formulations normally contain about 5% to about 25% active ingredients which may include surface-active agents such as heavy aromatic naphthas, kerosene or other petroleum fractions, or vegetable oils: and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active material enclosed in an inert porous shell which allows escape of the enclosed material to the surroundings at controlled rates. Encapsulated droplets are typically about 1 to 50 microns in diameter. The enclosed liquid typically constitutes about 50 to 95% of the weight of the capsule, and may includessolvent in addition to the active compund. Encapsulated granules are generally porous granules with porous membranes sealing the granule pore openings, retaining the active species in liquid form inside the granule pores. Granules typically range from 1 millimeter to 1 centimeter, preferably 1 to 2 millimeters in diameter. Granules are formed by extrusion. agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for herbicidal applications include simple solutions of the active ingredient in a solvent in which it is completely soluble at the desired concentration, such as acetone, alkylated napthalenes, xylene and other organic solvents. Pressurized sprays, wherein the active ingredient is dispersed in finely-divided form as a result of vaporization of a low boilnng dispersant solvent carrier, such as the Freons, may also be used.

Many of these formulations include wetting, dispersing or emulsifying agents. Examples are alkyl and alkylaryl sulfonates and sulfates and their salts; polyhydric alcohols: polyethoxylated alcohlls: esters and fatty amines. These agents when used normally comprise from 0.1% to 15% by weight of the formulation.

The compounds of the present invention are also useful when combined with other herbicides and/or defoliants, dessicants, growth inhibitors, and the like. These other materials can comprisefrom about 5% to about 95% of the active ingreients in the formulations. These combinations frequently provide a higher level of effectiveness in controlling weeds and often provide results unattainable with separate formulations of the individual herbicides.

Examples of other herbicides, defoliants, dessicants and plant growth inhibitors with which the compounds of this invention can be ombined are:

chlorophenoxy herbicides such as 2.4-D. 2.4.5-T. MCPA, MCPB, 2,4-DB, 2,4-DEB, 4-CPA, 2,4,5-TB, and silvex:

carbamate herbicides such as propham, chlrpropham, swep, and barban;

thiocarbamate and dithiocarbamate herbicides such as CDEC, metham-sodium, EPTC, diallate, PEBC, and vernolate;

substituted urea herbicides suchaas norea, dichloral urea, chloroxuron, cycluron, eenuron, monuron, monuron TCA, diuron, linuron, monolinuron neburon, buturon and trimeuuron;

symmetrical triazine herbicides such as simazine, chlorazine, desmetryne, norazine, ipazine, prometryn, atrazine, trietzine, simetone, prometone, propazine and ametryne;

chlorinated aliphatic acid herbicides such as TCA and dalapon;

chlorinated benzoic acid and phenylacetic acid herbicides such as 2,3,6-TBA, dicamba, tricamba, chloramben, fenac, PBA, 2-methoxy-3,6-dichlorohenylacetic acid, 3-methoxy-2,6-dichlorophenylacetec acid, 2-methoxy-3,5,6-trichlorophenylacetic acid and 2,4-dichloro-3-nitrobenzoic acid;

and such compounds as aminotriazole, maleic hydrazide, phenylmercury acetate, endothal, technical chlordane, DCPA, diquat, erbon, DNC, DNBP, dichlobenil, DPA, diphenamide, dipropalin, trifluralin, solan, dicryl, merphos, DMPA, DSMA, MSMA, potassium azide, acolein, benefin, bensulide, AMS, bromacil, 2-(3,4-dichoorophenyl)-4-methyl-1,2,4-oxazolidine-3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DDPA, PCA, sesone, terbacil, terbutol, TCBA, alachlor, nitralin, sodium tetraborate, calcium cyanamide, S,S,S-tributylphosphorotrithioate and propanil.

These formulations can be applied to the areas where control is desired by conventional methods. Dust and liquid compositions, for example, can be applied by the use of power-dusters, boom and hand sprayers and spray dusters. The formulations can also be applied from airplanes as a dust or a spray or by rope wick applications. To modify or control growth of germinating sedds or emerging seedlings, dust and liquid formulations can be distributed in the soil to a dephh of at least one-half inch below the soil surface or applied to the soil surface only, by spraying or sprinkling. The formulations can also be applied by addition to irrigation water. This permits penetration of the formulations into the soil together with the irrigation water. Dust compositions, granular compositions or liquid formulations applied to the surface of the soil can be distributed below the surface of the soil by conventional means such as discing, dragging or mixing operations.

The following are examples of typical formulations.

| 5% dust: | 5 parts active compound |
| --- | --- |
| | 95 parts talc |
| 2% dust: | 2 parts active compound |
| | 1 part highly dispersed silicic acid |
| | 97 parts talc |

These dusts are formed by mixing the components then grinding the mixture to the desired particle size.

| 5% granules: |
| --- |
| 5 parts active compound |
| 0.25 part epichlorohydrin |

| -continued |
| --- |
| 5% granules: |
| 0.25 part cetyl polyglycol ether |
| 3.5 parts polyethylene glycol |
| 91 parts kaolin (particle size 0.3–0.8 mm) |

Granules are formed by mixing the active compound with epichlorohydrin and dissolving the mixture in 6 parts of acetone. The polyethylene glycol and cetyl polyglyco ether are then added. The resultant solution is sprayed on the kaolin and the acetone evaporated in vacuo.

| wettable powders | |
| --- | --- |
| 70%: | 70 parts active compound |
| | 5 parts sodium dibutylnaphthylsulfonate |
| | 3 parts naphthalenesulfonic acid/phenolsulfonic acid/formaldehyde condensate (3:2:1) |
| | 10 parts kaolin |
| | 12 parts Champagne chalk |
| 40%: | 40 parts active compound |
| | 5 parts sodium lignin sulfonate |
| | 1 part sodium dibutylnaphthalenesulfonic acid |
| | 54 parts silicic acid |
| 25%: | 25 parts active compound |
| | 4.5 parts calcium lignin sulfate |
| | 1.9 parts Champagne chalk/hydroxyethyl cellulose (1:1) |
| | 1.5 parts sodium dibutylnaphthalenesulfonate |
| | 19.5 parts silicic acid |
| | 19.5 parts Champagne chalk |
| | 28.1 parts kaolin |
| 25%: | 25 parts active compound |
| | 2.5 parts isooctylphenoxy-polyethylene-ethanol |
| | 1.7 parts Champagne chalk/hydroxyethyl cellulose (1:1) |
| | 8.3 parts sodium aluminum silicate |
| | 16.5 parts kieselguhr |
| | 46 parts kaolin |
| 10%: | 10 parts active compound |
| | 3 parts of a mixture of sodium salts of saturated fatty alcohol sulfates |
| | 5 parts naphthalenesulfonic acid/formaldehyde condensate |
| | 82 parts kaolin |

These wetable powders are prepared by intimately mixing the active compounds with the additives in suitable mixers, and grinding the resulting mixtures in mills or rollers.

| 25% emulsifiable concentrate |
| --- |
| 25 parts active substance |
| 2.5 parts epoxidized vegetable oil |
| 10 parts of an alkylarylsulfonate/fatty alcohol polyglycol ether mixture |
| 5 parts dimethylformamide |
| 57.5 parts xylene |

What is claimed is:
1. A compound having the formula

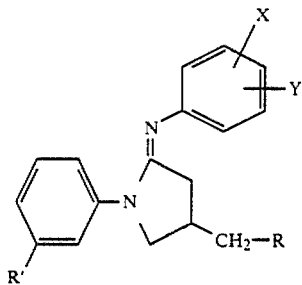

in which:
R is a member selected from the group consisting of H, halogen, and $C_1$-$C_4$alkyl;
R is a member selected from the group consisting of $CF_3$, $CH_3$, $CF_2CHF_2$, $OCF_2CHF_2$, $OCHF_2$, $OCF_3$, $SCH_3$, $S(O)CH_3$, $SO_2CH_3$, methoxyiminomethyl, methoxyimino-1-ethyl, benzoyloxyiminomethyl, and benzyloxyimino-1-ethyl; and
X and Y are independently selected from the group consisting of H, halogen, CN and $CF_3$.

2. A compound according to claim 1 in which:
R is a member selected from the group consisting of H halogen, and methyl;
R is $CF_3$; and
X and Y are independently selected from the group consisting of H, halogen, CN and $CF_3$.

3. compound according to claim 1 in which:
R is a member selected from the group consisting of H, halogen, and $C_1$-$C_4$ alkyl;
R is $CF_3$;
X is a member selected from the group consisting of H and halogen; and
Y is a member selected from the group consisting of H halogen, CN and $CF_3$.

4. A compound according to claim 1 in which:
R is a member selected from the group consisting of H, chloro, bromo, fluoro, and methyl;
R is $CF_3$; and
X and Y are independently selected from the group consisting of H chloro, bromo, fluoro, CN and $CF_3$.

5. A compound according to claim 1 in which:
R is a member selected from the group cosisting of H, chloro, fluoro, and methyl; R is $CF_3$; and
X and Y are independently selected from the group consisting of H, chloro, fluoro, CN and $CF_3$.

6. A compound according to claim 1 in which:
R is a member selected from the group consisting of H, chloro, fluoro, and methyl;
R is $CF_3$;
X is a member selected from the group consisting of H chloro, and fluoro; and
Y is a member selected from the group consisting of H, chloro, fluoro, CN and $CF_3$.

7. A compound according to claim 1 in which:
R is a member selected from the group consisting of chloro and methyl;
R' is $CF_3$;
X is a member selected from the group consisting of H, cloro, and fluoro; and
Y is a member seletted from the group consisting of H, chloro, fluoro, CN and $CF_3$.

8. A compound according to claim 1 in which:

R is a member selected from the group consisting of chloro and methyl;
R is $CF_3$;
X is H: and
Y is a member selected from the group consisting of chloro, fluoro, CN and $CF_3$.

9. A compound according to claim 1 in which R is methyl, R' is $CF_3$, X is H, and Y is 4-CN.

10. A compound according to claim 1 in which R is methyl, R' is $CF_3$, X is H, and Y is 4-F.

11. An herbicidal composition comprising:
(a) an herbicidally effective amount of a compound having the formula

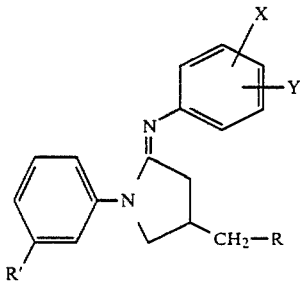

in which:
R is a member selected from the group consisting of H, halogen, and $C_1$-$C_4$ alkyl;
R' is a member selected from the group consisting of $CF_3$, $CH_3$, $CF_2CHF_2$, $OCF_2CHF_2$, $OCHF_2$, $OCF_3$, $SCH_3$, $S(O)CH_3$, $SO_2CH_3$, mthoxyiminomethyl, methoxyimino-1-ethyl, benzoyloxyiminomethyl.
and benzoyloxyimino-1-ethyl and X and Y are independently selected from the group consisting of H, halogen, CN and $CF_3$; and
(b) an herbicidally suitable inert diluent or carrier.

12. An herbicidal composition according to claim 11 in which:
R is a member selected from the group consisting of H, halogen, and methyl;
R' is $CF_3$; an
X and Y are independently selected from the group consisting of H, halogen, CN and $CF_3$.

13. An herbicidal composition according to claim 11 in which:
R is a member selected from the group consisting of H, halogen, and $C_1$-$C_4$ alkyl;
R is $CF_3$;
X is a member selected from the group consisting of H and halogen: and
Y is a member selected from the group consisting of H, halogen, CN and $CF_3$.

14. An herbicidal composition according to claim 11 in which:
R is a member selected from the group consisting of H, chloro, bromo, fluoro, and methyl;
R' is $CF_3$; and
X and Y are independently selected from the group consisting of H, chloro, bromo, fluoro, CN and $CF_3$.

15. An herbicidal composition according to claim 11 in which:
R is a member selected from the group consisting of H, chloro, fluoro, and methyl;
R is $CF_3$; and X and Y are independently selected from the group consisting of H, chloro, fluoro, CN and CF$_3$.

16. An herbicidal composition according to claim 11 in which:
R is a member selected from the group consisting of H, chloro, fluoro, and methyl;
R' is CF$_3$;
X is a member selected from the group consisting of H, chloro, and fluoro; and
Y is a member selected from the group consisting of H, chloro, fluoro, CN and CF$_3$.

17. An herbicidal composition according to claim 11 in which:
R is a member selected from the group consisting of chloro and methyl;
R' is CF$_3$;
X is a member selected from the group consisting of H, chloro, and fluoro; and
Y is a member selected from the group consisting of H, chloro, fluoro, CN and CF$_3$.

18. An herbicidal composition according to claim 11 in which:
R is a member selected from the group consisting of chloro and methyl;
R' is CF$_3$;
X is H: and
Y is a member selected from the group consisting of chloro, fluoro, CN and CF$_3$.

19. An herbicidal composition according to claim 11 in which R is methyl, R' is CF$_3$, X is H, and Y is 4-CN.

20. An herbicidal composition according to claim 11 in which R is methyl, R' is CF$_3$, X is H, and Y is 4-F.

21. A method of controlling undesirable vegetation comprising applying to said vegetation or to the locus thereof an herbicidally effective amount of a compound having the formula

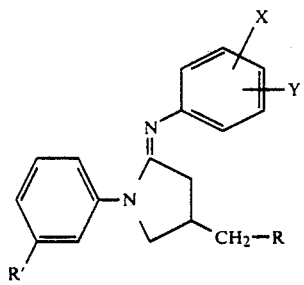

in which:
R is a member selected foom the group consisting of H, halogen, and C$_1$-C$_4$ alkyl;
R' is a member selected from the group consisting of CF$_3$, CH$_3$, CF$_2$CHF$_2$, OCF$_2$CHF$_2$, OCHF$_2$, OCF$_3$, SCH$_3$, S(O)CH$_3$, SO$_2$CH$_3$, methoxyiminomethyl, methoxyimino-1-ethyl, benzoyloxyiminomethyl, and benzoyloxyimino-1-ethyl; and
X and Y are independently selected from the group consisting of H, halogen, CN and CF$_3$.

22. A method according to claim 21 in which:
R is a member selected from the group consisting of H, halogen, and methyl;
R' is CF$_3$; and
X and Y are independently selected from the group consisting of H, halogen, CN and CF$_3$.

23. A method according to claim 21 in which:
R is a member selected from the group consisting of H, halogen, and C$_1$-C$_4$ alkyl;
R' is CF$_3$;
X is a member selected from the group consisting of H and halogen: and
Y is a member selected from the group consisting of H, halogen, CN and CF$_3$.

24. A method according to claim 21 in which:
R is a member selected from the group consisting of H, chloro, bromo, fluoro, and methyl;
R' is CF$_3$; and
X and Y are independently selected from the group consisting of H, chloro, bromo, fluoro, CN and CF$_3$.

25. A method according to claim 21 in which:
R is a member selected from the group consisting of H, chloro, fluoro, and methyl;
R' is CF$_3$; and
X and Y are independently selected from the group consisting of H chloro, fluoro, CN and CF$_3$.

26. A method according to claim 21 in which:
R is a member selected from the group consisting of H, chloro, fluoro, and methyl;
R' is CF$_3$;
X is a member selected from the group consisting of H, chloro, and fluoro; and
Y is a member selected from the group consisting of H, chloro, fluoro, CN and CF$_3$.

27. A method according to claim 21 in which:
R is a member selected from the group consisting of chloro and methyl;
R' is CF$_3$;
X is a member selected from the group consisting of H, chloro, and fluoro; and
Y is a member selected from the group consisting of H, chloro, fluoro, CN and CF$_3$.

28. A method according to claim 21 in which:
R is a member selected from the group consisting of chloro and methyl;
R' is CF$_3$;
X is H; and
Y is a member selected from the group consisting of chloro, fluoro, CN and CF$_3$.

29. A method according to claim 21 in which R is methyl, R is CF$_3$, X is H, and Y is 4-CN.

30. A method according to claim 21 in which R is methyl, R' is CF$_3$, X is H, and Y is 4-F.

* * * * *

UNITED STATES PATENT AND TRADEMARK OFFICE
CERTIFICATE OF CORRECTION

PATENT NO. : 4,909,834
DATED : March 20, 1990
INVENTOR(S) : Frank X. Woolard

It is certified that error appears in the above-indentified patent and that said Letters Patent is hereby corrected as shown below:

In Column 11, lines 17, 27, 34, 42, 48, 54, "R" should read --R'--.

In Column 12, lines 3, 51, 68, "R" should read --R'--.

In Column 11, line 26, insert a comma after "H".

In Column 11, line 30, insert "A" before the word "compound".

In Column 11, line 38, insert a comma after "H".

In Column 11, line 44, insert a comma after "H".

In Column 11, line 65, "cloro" should read --chloro--.

In Column 11, line 66, "seletted" should read --selected--.

In Column 12, line 4, "H:" should read --H;--.

UNITED STATES PATENT AND TRADEMARK OFFICE
CERTIFICATE OF CORRECTION

PATENT NO. : 4,909,834
DATED : March 20, 1990
INVENTOR(S) : Frank X. Woolard

It is certified that error appears in the above-indentified patent and that said Letters Patent is hereby corrected as shown below:

Column 12, line 33, "mthox-" should read --methox--.
Column 12, line 35, delete the period after "yiminomethyl" and insert a comma--.
Column 12, line 36, insert a semi-colon after the word "ethyl".
Column 13, line 55, "foam" should read --from--.
Column 14, line 31, insert a comma after "H"--.
Column 14, line 56, "R" should read --R'--.

Signed and Sealed this

Seventh Day of June, 1994

Attest:

BRUCE LEHMAN

*Attesting Officer*    Commissioner of Patents and Trademarks